United States Patent
O'Dea et al.

(10) Patent No.: US 8,554,826 B2
(45) Date of Patent: Oct. 8, 2013

(54) METHOD AND SYSTEM FOR XML MESSAGE BASED TRANSACTIONS ON A MEDICAL DIAGNOSTIC SYSTEM

(75) Inventors: Paul Joseph O'Dea, Muskego, WI (US); Scot David Prichard, Muskego, WI (US)

(73) Assignee: General Electric Company, Schenectady, NY (US)

( * ) Notice: Subject to any disclaimer, the term of this patent is extended or adjusted under 35 U.S.C. 154(b) by 1648 days.

(21) Appl. No.: 11/215,221

(22) Filed: Aug. 30, 2005

(65) Prior Publication Data
US 2007/0050780 A1    Mar. 1, 2007

(51) Int. Cl.
*G06F 15/16* (2006.01)
*G06F 3/00* (2006.01)
*A61B 8/00* (2006.01)

(52) U.S. Cl.
USPC ............ 709/201; 709/236; 719/313; 600/437

(58) Field of Classification Search
USPC ............ 600/437; 709/203, 236, 201; 719/313
See application file for complete search history.

(56) References Cited

U.S. PATENT DOCUMENTS

| | | | | |
|---|---|---|---|---|
| 6,306,089 B1 * | 10/2001 | Coleman et al. | ............ | 600/437 |
| 6,510,434 B1 * | 1/2003 | Anderson et al. | ............ | 707/100 |
| 7,054,901 B2 * | 5/2006 | Shafer | ............ | 709/203 |
| 7,072,985 B1 * | 7/2006 | Lev-Ami et al. | ............ | 709/246 |
| 7,162,534 B2 * | 1/2007 | Schleiss et al. | ............ | 709/232 |
| 7,281,205 B2 * | 10/2007 | Brook | ............ | 715/237 |
| 2002/0010679 A1 * | 1/2002 | Felsher | ............ | 705/51 |
| 2002/0023172 A1 * | 2/2002 | Gendron et al. | ............ | 709/238 |
| 2002/0065900 A1 * | 5/2002 | Dor et al. | ............ | 709/217 |
| 2004/0141661 A1 * | 7/2004 | Hanna et al. | ............ | 382/305 |
| 2004/0249667 A1 * | 12/2004 | Oon | ............ | 705/2 |
| 2007/0083615 A1 * | 4/2007 | Hollebeek et al. | ............ | 709/218 |

OTHER PUBLICATIONS

Adi Shavit and Arnaud Brejeon, XMLParam: An XML-Based Parameter and setting I/O Framework, May 2004, 5 pages.

* cited by examiner

*Primary Examiner* — Rupal Dharia
*Assistant Examiner* — Robert B McAdams
(74) *Attorney, Agent, or Firm* — The Small Patent Law Group; Dean D. Small (57) ABSTRACT

A method and system for sending and receiving XML message based transactions between a client and software components of a medical imaging system comprises forming a message with a client. The message comprises a header section and a data section and is sent to a first component. The first component receives the message and executes a transaction based on the message.

21 Claims, 8 Drawing Sheets

METHOD AND SYSTEM FOR XML MESSAGE BASED TRANSACTIONS ON A MEDICAL DIAGNOSTIC SYSTEM

BACKGROUND OF THE INVENTION

This invention relates generally to messaging within a medical diagnostic system, and more particularly, to reducing the number of calls needed to accomplish a transaction and to increasing the transaction integrity.

Medical diagnostic systems, such as Ultrasound, Computed Tomography (CT), X-ray, Fluoroscopy, Positron Emission Tomography (PET) and Magnetic Resonance Imaging (MRI), use many different software components to accomplish tasks and transactions. It is often necessary to send numerous messages or calls between software components in order to complete a single transaction.

Transactions which take a number of calls to complete can cause reliability problems. For example, a first software component may send multiple name value(s) pairs to a second software component via an automatic call for each pair, followed by an execute command. Alternatively, the first software component may send a start transaction call, followed by multiple name value(s) pairs, followed by a execute transaction call. The retrieval of name value(s) pairs are also accomplished in the same manner. Any one call which is not received or is interrupted by other messages or priorities may cause the entire transaction to fail. Alternatively, additional traffic between software components may be generated and the time needed to complete a transaction may increase.

The messaging scheme can be cumbersome and unique to each software component, thus difficult to document and can cause the system to be fragile. Also, it can be difficult to integrate new or modified software components which are desired for additional functionality. For example, when integrating existing third party software packages, the source code often must be modified to enable the software components to talk to one another.

Therefore, a need exists for a messaging system within the medical imaging systems which minimizes the number of messages needed to complete a transaction, thus improving the reliability of the system and decreasing the time needed for each transaction, and which allows for additional software components to be easily integrated into the medical imaging system. Certain embodiments of the present invention are intended to meet these needs and other objectives that will become apparent from the description and drawings set forth below.

BRIEF DESCRIPTION OF THE INVENTION

In one embodiment, a method for sending and receiving XML message based transactions between a client and software components of a medical imaging system comprises forming a message with a client. The message comprises a header section and a data section and is sent to a first component. The first component receives the message and executes a transaction based on the message.

In another embodiment, a system for sending and receiving XML message based transactions within an ultrasonic imaging system comprises a front-end for transmitting ultrasonic signals and receiving echoes based on the ultrasonic signals. The system further comprises processing architecture comprising components for processing the echoes and an input device for inputting data. A computer comprises a microprocessor and a memory which stores data input from the input device. The computer further comprises a storage device for storing software programs comprising a client and a client XML messaging wrapper for generating XML message based transactions. The software programs further comprise at least a first component and a first XML messaging wrapper for receiving and processing the XML message based transactions. The client XML messaging wrapper and the first XML messaging wrapper comprise functions for reading and writing data in XML format to create and process a first set of XML message based transactions.

In another embodiment, a method for sending and receiving XML message based transactions within a medical imaging system comprises building a message with a client and an XML message wrapper to be sent from the client to a first software component. The message requests completion of a transaction and comprises a header section and a data section formed of XML tags. The XML messaging wrapper comprises functions for reading and writing data in XML format. A text based representation of the message is created and sent to the first software component.

The foregoing summary, as well as the following detailed description of certain embodiments of the present invention, will be better understood when read in conjunction with the appended drawings. It should be understood that the present invention is not limited to the arrangements and instrumentality shown in the attached drawings.

DETAILED DESCRIPTION OF THE INVENTION

Figure 1:
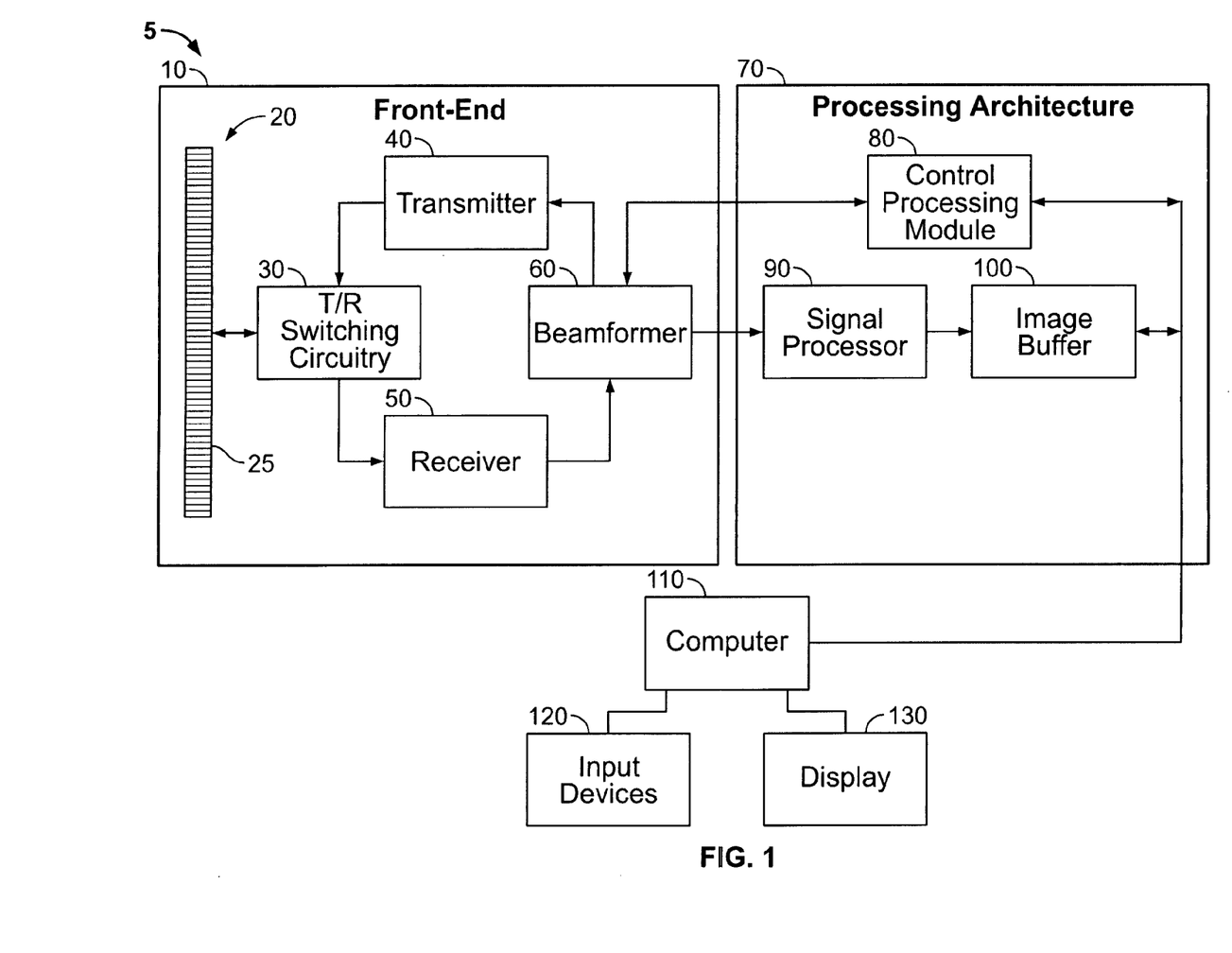
FIG. 1 is a schematic block diagram of an ultrasound system for sending and receiving message based transactions in accordance with an embodiment of the present invention.

FIG. 1 is a schematic block diagram of an ultrasound system 5 for sending and receiving message based transactions in accordance with an embodiment of the present invention. Transactions which previously required multiple calls to execute are replaced by a single message which contains the entire transaction, herein called a message based transaction. It should be understood that the ultrasound system 5 is an example of a medical imaging system, and that other types of medical imaging systems (e.g. CT, MRI, X-ray, PET) may also utilize message based transactions.

A front-end 10 comprises a transducer array 20 (comprising a plurality of transducer array elements 25), transmit/receive switching circuitry 30, a transmitter 40, a receiver 50, and a beamformer 60. Processing Architecture 70 comprises a control processing module 80, a signal processor 90 and an image buffer 100. A computer 110 is interconnected with the processing architecture 70. A display 130 and one or more input devices 120, such as a keyboard, trackball, touchscreen and the like are connected with the computer 110.

To generate a transmitted ultrasound beam, the control processing module 80 sends command data to the beamformer 60, telling the beamformer 60 to generate transmit parameters to create a beam having a defined shape, point of origin, and steering angle. The transmit parameters are sent from the beamformer 60 to the transmitter 40. The transmitter 40 drives the transducer elements 25 within the transducer array 20 through the T/R switching circuitry 30 to emit pulsed ultrasonic signals into a body.

The ultrasonic signals are back-scattered from structures in the body, like blood cells or muscular tissue, to produce echoes which return to the transducer array 20. The transducer elements 25 convert the ultrasound energy from the backscattered waves into received electrical signals. The received electrical signals are routed through the T/R switching circuitry 30 to the receiver 50, which amplifies and digitizes the received signals and provides other functions such as gain compensation.

The digitized received signals are sent to the beamformer 60. According to instructions received from the control processing module 80, the beamformer 60 performs time delaying and focusing to create received beam signals. The received beam signals are sent to the signal processor 90, which prepares frames of ultrasound information. The frames may be stored in an image buffer 100, which may comprise any known storage medium.

Figure 2:
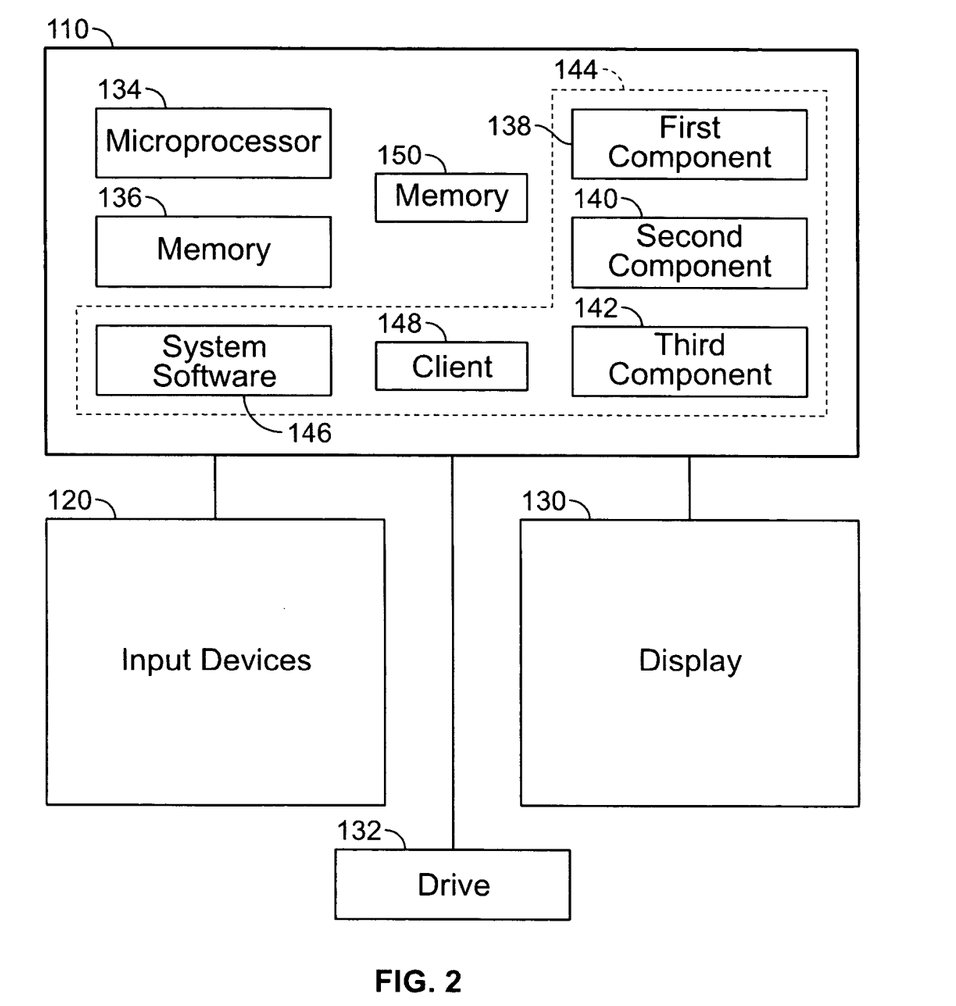
FIG. 2 illustrates the computer, input devices and display of the ultrasound system using message based transactions in accordance with an embodiment of the present invention.

FIG. 2 illustrates the computer 110, input devices 120 and display 130 of the ultrasound system 5 using message based transactions in accordance with an embodiment of the present invention. As stated previously, the use of message based transactions is not limited to the ultrasound system 5, and may be used in other imaging systems. The computer 110 may be a personal computer or other apparatus for processing, receiving and outputting data. The computer 110 is also interconnected with a drive 132 which may be external, such as, for example, a DVD, CD, or Optical drive.

The computer 110 comprises components such as a microprocessor 134 and memories 136 and 150. Memory 136 may be a short term memory for temporarily storing data input from the input devices 120, while the memory 150 may be a drive having a large capacity for storing patient data. First, second and third components 138, 140 and 142 may be stored on a storage device 144, such as a hard drive. Alternatively, the components 138-142 may be stored on a separate system or drive (not shown) interconnected with a direct link to the computer 110. System software 146 refers to applications, interface utilities, and other code typically utilized by the ultrasound system 5. A client 148 is the software component of the system software 146 which prepares message based transactions and interfaces with the components 138-142. The system software 146 and client 148 may also be stored on the storage device 144, in the memory 150 or on a separate drive.

The components 138-142 comprise software programs or applications designed to perform a specific transaction or set of transactions other than the scan acquisition and processing accomplished by the front-end 10 and processing architecture 70. For example, the first component 138 may be a program which allows a user to create a new patient by using input devices 120 to input data, such as into a form displayed on the display 130. The second component 140 may be a measurement package for performing measurements of a liver, heart, fetus and the like, while the third component 142 may be a program for storing selected data and files to the external drive 132. Therefore, the first, second and third components 138-142 perform different sets of transactions. The client 148 sends the message based transaction to the appropriate component 138-142 with one call. It should be understood that many different components 138-142 are provided on the computer 110.

The message based transactions support out-of-process communication and out-of-process third party packages. Therefore, message based transactions may be accomplished by communicating between two distinct programs or components on the same computer or system, and also by communicating between two distinct programs or components located on separate computers or systems.

Figure 3:
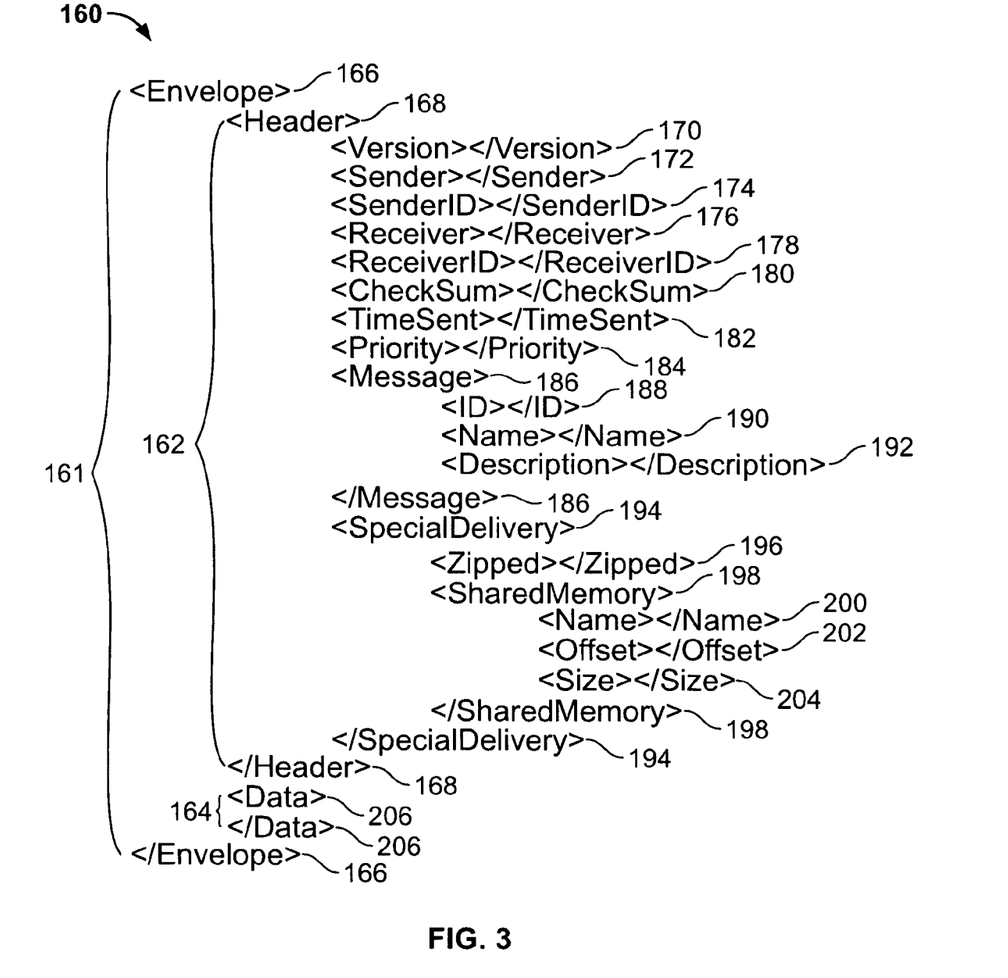
FIG. 3 illustrates an Extensible Markup Language (XML) message definition for messages used in message based transactions in accordance with an embodiment of the present invention.

FIG. 3 illustrates an Extensible Markup Language (XML) message definition 160 for messages used in message based transactions in accordance with an embodiment of the present invention. XML is used by the system 5 to implement a message based system that both improves transaction-processing time and enforces transaction integrity. One call replaces the multiple calls previously needed to send a transaction. Reducing the number of calls necessary to process a transaction enables more efficient transaction management and ensures transaction integrity.

The XML message definition 160 is an envelope in which the data of the transaction is placed. The XML message definition 160 provides the structure and the information to route the data correctly, such as to the desired client 148 and components 138-142. It is important to note that the data content of the message is left open to the sender and receiver of the message. Therefore, the <data> section (further discussed below) is an open definition and allows the sender and receiver to define the contract which describes the transaction data.

In FIG. 3, an XML message is formed out of a set of calls, and thus each message based transaction is an XML string. Free-form text based transactions can be used to define any transaction that can be described in a string. This allows dissimilar client and server software modules, implementations, and technologies.

A wrapper class, herein referred to as XML messaging wrapper, is used by the client 148 and the components 138-142 to insert and extract pieces in the message. In other words, the XML messaging wrapper contains the functions needed to read and write data in XML format to create and process XML message based transactions. The client 148 can send a finite set of XML message based transactions to each of the components 138-142. Each of the components 138-142 knows how to handle and process their own set of XML message based transactions. The system 5 may utilize a single defined XML messaging wrapper for the client 148 and components 138-142, or each of the components 138-142 may have a specific XML messaging wrapper comprising a subset of the functions utilized by the client 148. The <data> section is, or can be, unique to each XML message based transaction. The interpretation of the tags in the XML message indicates to the client 148 and component 138-142 how to process the <data> section.

A header section 162 and a data section 164 are within an XML envelope 161. The XML message definition 160 provides a detailed description of the header section 162, which is required for all messages. It should be understood that the illustrated header section 162 is exemplary only, and is not limited to the embodiment shown. Having a predefined header section 162 allows the client 148 to easily communicate with components 138-142, as well as other components which may be provided in the future, such as third-party software packages.

Following the header section 162 is the data section 164. The content of the data section 164 is message dependant and is defined by the individual component 138-142, depending upon the needs of the application of the component 138-142. As stated previously, the data section 164 is intentionally left to the application code of the component 138-142 as it is deemed to be part of the contract between the sender and receiver, much like the data in a network message.

The following discussion refers to elements used within the XML message definition 160. Each element begins with a start-tag and ends with an end-tag, and the elements are indicated by name and item number in FIG. 3. The elements may have an assigned value type, as is known in the art, such as string, integer, unsigned integer, and the like. Optionally, a default value may be inserted by the client 148.

Envelope 166 indicates the beginning and end of the message, and Header 168 indicates the beginning and end of the header section 162. Neither the Envelope 166 nor the Header 168 has a defined value type. Version 170 (a string) indicates the version of the XML message header being used, and is implicitly inserted by the client 148. Sender 172 (a string) comprises the name of the sender, and SenderID 174 (an integer) identifies the sender. Receiver 176 (a string) comprises the name of the receiver, and ReceiverID 178 (an integer) identifies the receiver. For example, the sender may be the client 148 and the receiver may be the first component 138.

CheckSum 180 (an unsigned integer) is the CRC checksum of the data for receiver validation. TimeSent 182 (an unsigned integer) is the time the message was sent by the sender, and priority 184 (an integer) indicates message priority.

Message 186 indicates the beginning and end of a message within the header section 162. ID 188 (an integer), Name 190 and Description 192 (both strings) are used to uniquely identify and describe the XML message based transaction. SpecialDelivery 194 indicates the beginning and end of a section of instructions describing alternative message delivery instructions, such as Zipped 196 (an integer) and SharedMemory 198. SharedMemory 198 may be used when large messages are being delivered, comprising a Name 200 (a string) of the shared memory, an Offset 202 (an unsigned integer) into the shared memory where the data resides, and a Size 204 (an unsigned integer) of the block of shared code. By way of example only, SharedMemory 198 may be used to indicate data stored in the memory 150.

The data section 164 follows the header section 162 within the envelope 166. Data 206 is the container for the message content, and is defined between the sender and receiver, such as between the client 148 and the first component 138.

Some of the tags are required, such as Envelope 166, Header 168, Version 170, Sender 172, SenderID 174, Receiver 176, ReceiverID 178, TimeSent 182, Message 186, ID 188, Name 190, Description 192, and Data 206. Other tags are optional and may or may not be included. If any required tags are defaulted (i.e. not present, have an incorrect data type inserted, or occur multiple times), when the XML is extracted to a BSTR (basic or binary string) or text string for transmission, an error will be generated and the BSTR will remain empty. Other text strings may be used, such as ASCII, Unicode, and the like, and may be referred to as a text based representation.

Figure 4:
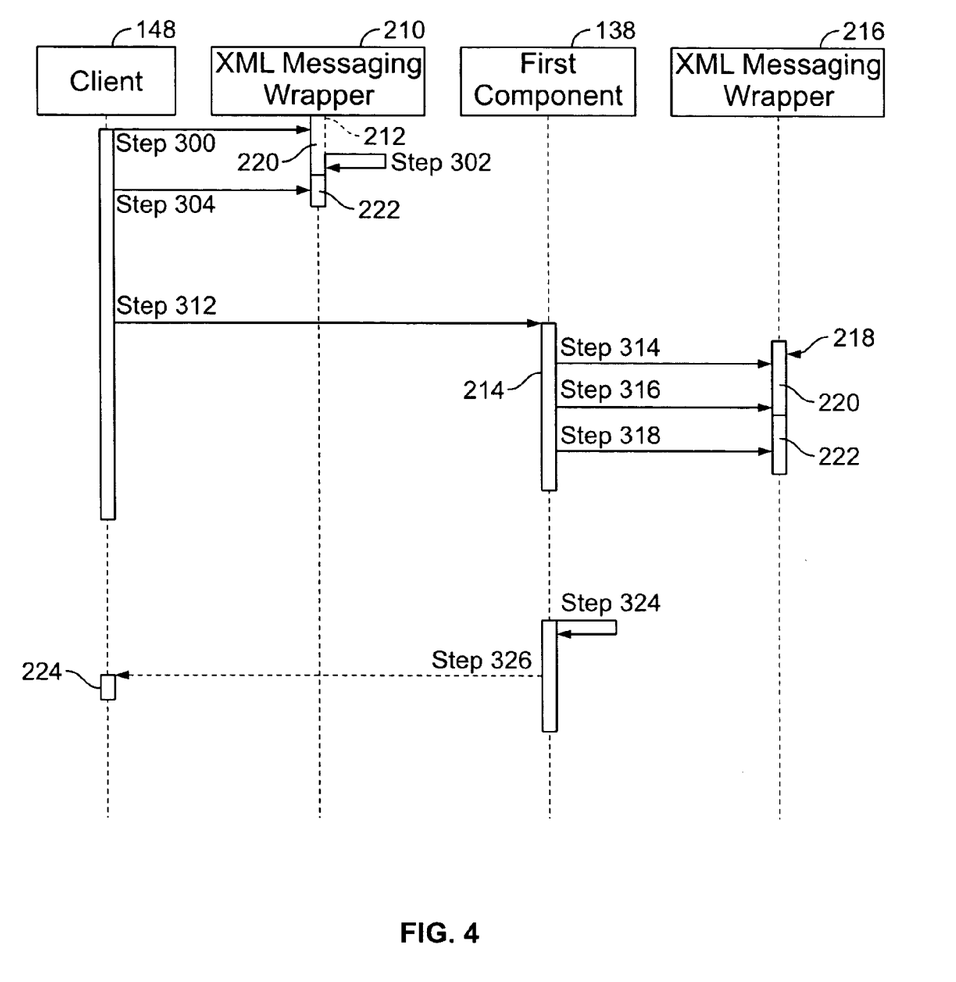
FIG. 4 illustrates a diagram of an XML message based transaction being created by the client and received by the first component in accordance with an embodiment of the present invention.
Figure 5:
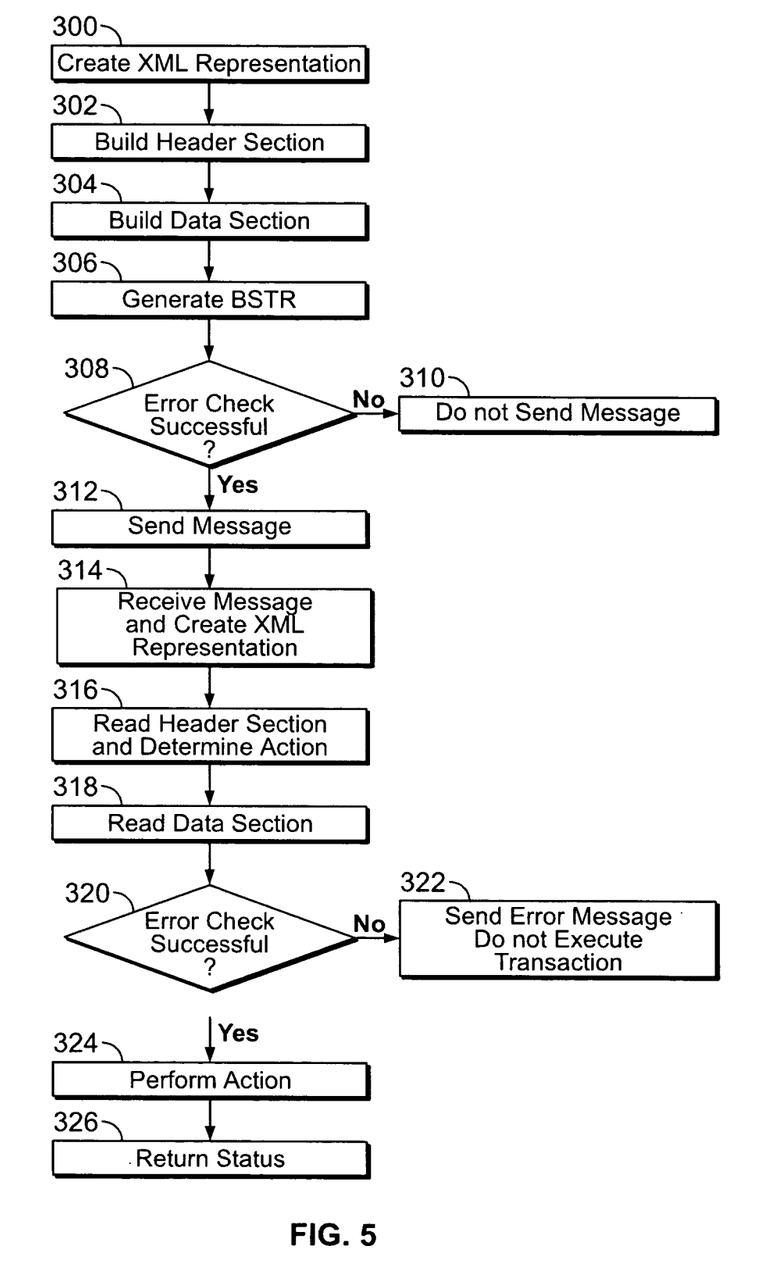
FIG. 5 illustrates a flow chart of steps to accomplish the XML message based transaction of FIG. 4 in accordance with an embodiment of the present invention.

FIG. 4 illustrates a diagram of an XML message based transaction being created by the client 148 and received by the first component 138 in accordance with an embodiment of the present invention. XML messaging wrappers 210 and 216 indicate the XML messaging wrapper being used by the client 148 and component 138. The code for XML messaging wrappers 210 and 216 is decoupled from the application code, allowing easy future modification of the wrapper. XML messaging wrappers 210 and 216 provide a mechanism to integrate transaction based processing into existing software systems. Internal and external software modules are decoupled to ease module integration, replacement and modification. The Open System design also allows easier communication with third party software packages, allowing third party software packages to be used as value added features for the system 5. FIG. 5 illustrates a flow chart of steps to accomplish the XML message based transaction of FIG. 4 in accordance with an embodiment of the present invention. FIGS. 4 and 5 will be discussed together.

The XML messaging wrapper 210 and 216 is the wrapper class responsible for creating the XML message based transactions sent between the client 148 and the first component 138, and provides the functionality required by both the client 148 and the first component 138. XML messaging wrapper 210 and 216 aggregates the parameters used (ParamIO) to avoid inheritance and to provide a lightweight interface. XML messaging wrapper 210 and 216 also provide the ability to generate a BSTR from the XML representation, and to create an XML representation from a BSTR, while the transportation of the XML messages (the text based representation) is the responsibility of the application.

In FIG. 4, the client 148 is creating a message to send to the first component 138. Information may be written to the XML envelope 161 using method setHeader. Similarly, information from the header section 162 is retrieved using method getHeader. Depending on the message, the data section 164 can be written using method setData, and the information in the data section can be retrieved using method getData. It should be understood that other methods may be used.

In step 300, the client 148 uses the XML messaging wrapper 210 to create an XML representation 212 to package the XML envelope 161. In step 302, the client 148 builds header section 220, such as by using method setHeader. The header section 220 is built with the required and optional tags as discussed previously in FIG. 3. In step 304, the client 148 builds data section 222, such as by using method setData. As stated previously, the data section 222 is defined between the client 148 and the first component 138. The data section 222 may comprise a data string of information, such as patient identification data, or may be XML represented by a character string. Steps 302 and 304, building the header and data sections 220 and 222, may be referred to as constructing an XML tree.

In step 306, the XML messaging wrapper 210 generates message 214, which is a BSTR or a text based representation of the XML tree. In step 308, XML messaging wrapper 210 performs error checking and verifies that all required tags are present in the message 214. It should be understood that steps 306 and 308 may be accomplished simultaneously. If all of the required tags are not present, flow passes to step 310 and the message 214 is not sent. If error checking fails, the client 148 will perform an appropriate action or response, which may not be the same for every message. For example, the message may be regenerated, a failure status message may be displayed on the display 130, or the error may be logged in a file for later analysis. If all of the required tags are present in step 308, flow passes to step 312, and the message 214 is sent by the client 148 to the first component 138.

Premature error messages are prevented by checking the header section 220 and data section 222 for validity when the XML messaging wrapper 210 attempts to extract the BSTR representation of the XML tree. SetHeader and/or setData may be used to manually insert and/or change information in the XML tree, and therefore no checks are performed during the construction of the XML tree, or while performing steps 302 and 304.

In step 314, the first component 138 receives the message 214 and uses XML messaging wrapper 216 to create an XML representation 218. In step 316, the first component 138 reads the header section 220 and then determines the action to be taken. When the first component 138 is ready to take the action, in step 318 the first component 138 reads the data section 222.

Before an XML message based transaction is executed, error checking is performed in step 320 to verify that the message 214 contains data in the data section 222 and a valid header in the header section 220. If a tag is not required, then the first component 138 will skip over the tag. If there is no data present in the data section 222, the header section 220 is invalid, or a required tag does not exist, flow passes to step 322. In step 322, the first component 138 does not execute the transaction. Optionally, the first component 138 may send an error message to the client 148

If the message 214 is valid, flow passes from step 320 to step 324, and the first component 138 performs the action. In step 326, the first component 138 returns a status message 224 to the client 148. The status message 224 indicates whether the action was performed successfully or not.

Figure 6:
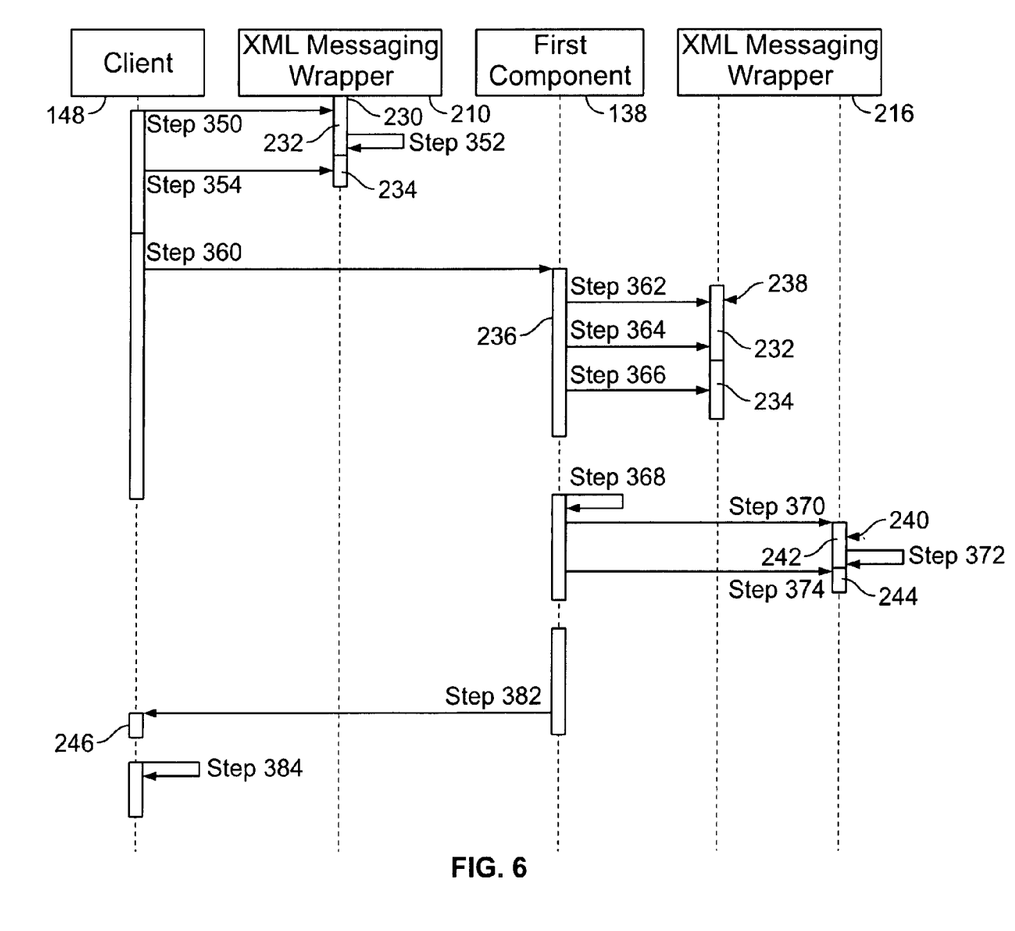
FIG. 6 illustrates a diagram of how the client requests and receives data from the first component using XML message based transactions in accordance with an embodiment of the present invention.
Figure 7:
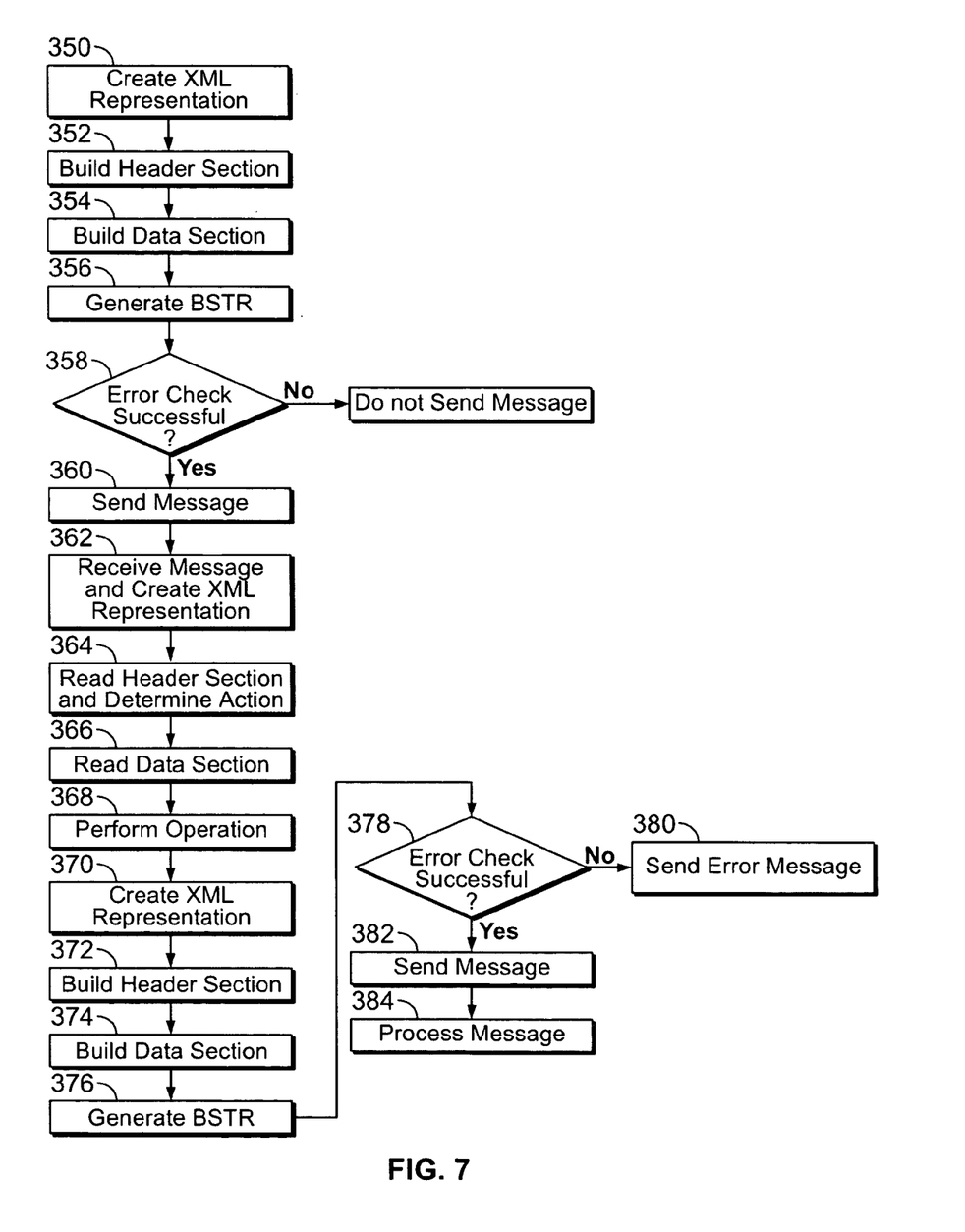
FIG. 7 illustrates a flow chart of steps to accomplish the XML message based transactions of FIG. 6 in accordance with an embodiment of the present invention.

FIG. 6 illustrates a diagram of how the client 148 requests and receives data from the first component 138 using XML message based transactions in accordance with an embodiment of the present invention. FIG. 7 illustrates a flow chart of steps to accomplish the XML message based transactions of FIG. 6 in accordance with an embodiment of the present invention. FIGS. 6 and 7 will be discussed together.

In step 350, the client 148 uses XML messaging wrapper 210 to create an XML representation 230. In step 352, the client 148 builds header section 232 with the necessary information. In step 354, the client 148 builds data section 234 with the client's request for data. In step 356, the XML messaging wrapper generates message 236, which is a BSTR of the XML tree. In step 358, XML messaging wrapper 210 may perform error checking to verify that all required tags are present, as discussed previously.

In step 360, the client 148 sends the message 236 to the first component 138, which uses XML messaging wrapper 216 to create XML representation 238 to parse the XML in step 362. In step 364, the first component 138 reads the header section 232 to determine what action to take. After the action is determined, in step 366 the first component 138 reads the data section 234. In step 368, the first component 138 performs the requested operation.

In step 370, the first component 138 uses XML messaging wrapper 216 to create XML representation 240. The first component 138 builds a header section 242 in step 372, and in step 374 the first component 138 builds data section 244. In this example, the information that the first component 138 gathered from performing the client's request is used to build the data section 244.

In step 376, the XML messaging wrapper 216 generates message 246, which is a BSTR of the XML tree. In step 378, an error check is performed to verify that the message 246 contains data in the data section 244 and a valid header in the header section 242. If no data is present, the header is invalid, or a required tag is not present, flow passes to step 380 and an error message is returned to the client 148.

If the message 246 is valid, flow passes from step 378 to step 382, and the first component 138 sends the message 246 to the client 148. In step 384 the client 148 processes the received data as previously discussed, and may also include error and validity checking.

A number of different errors may be generated. Errors may be displayed to the user on the display 130 and/or written to an error log (not shown). By way of example and not limitation, if the header section is not well-formed or a required tag does not exist, the user may be informed of the error. If data is not present or a required tag does not exist within the data section, the user may be informed of the error. If the user attempts to write a tag to the header section which does not belong in the header section, or attempts to write data to the header section, the tag is not written to the XML tree and the user may be informed of the error.

In the event the user writes data to a tag with one type (e.g. writeHeader("Sender", stringVal) and then attempts to read that data into a variable of a different type (e.g. readHeader ("Sender", intVal)), readHeader will return false indicating the data inside the tag could not be read and the user may be informed of the error. If the user attempts to writeHeader with an empty tag (e.g. writeHeader("",someVal)), writeHeader will return false because the empty string is not a valid tag, and the user may be informed of the error.

Figure 8:
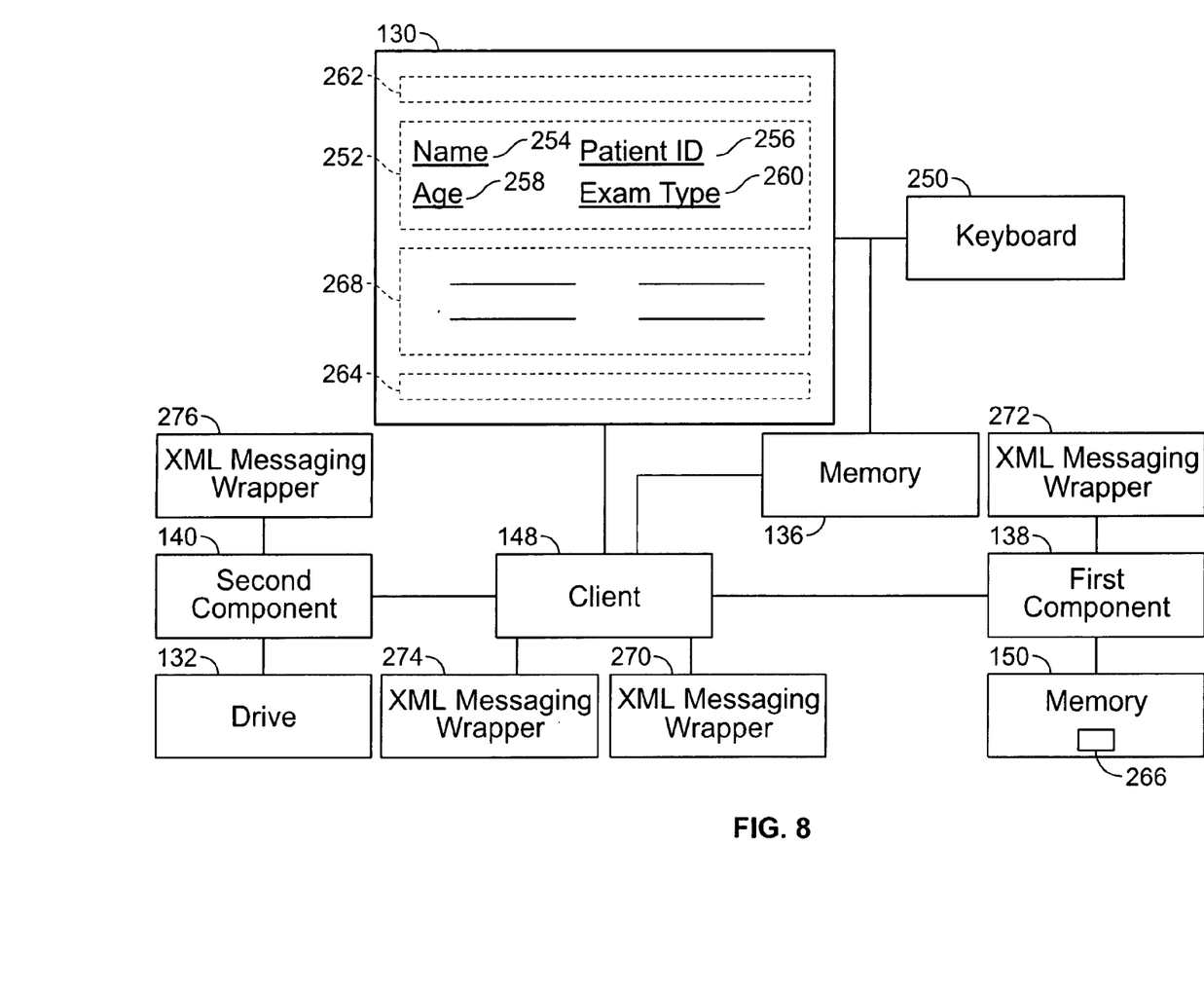
FIG. 8 illustrates an example of the system using XML message based transactions in accordance with an embodiment of the present invention.

FIG. 8 illustrates an example of the system 5 using XML message based transactions in accordance with an embodiment of the present invention. Using XML message based transactions, a single transaction is created and sent. The single transaction has all of the necessary information to complete what used to require multiple calls.

A user may select a key on a keyboard 250 or other user input device 120 which notifies the client 148 that the user wishes to create a new patient. A form 252 is displayed on the display 130. Forms are often used to gather multiple data, such as to create a patient record and input measurements. The form 252 has multiple fields for the user to input data into, such as Name 254, Patient ID 256, Age 258, and Exam Type 260. Each of the fields has a defined data type.

Previously, multiple calls were sent by the client 148 to the first component 138 when creating a new patient as the user entered data into the form 252. A first call tells the first component 138 to create a new patient record, a second call sends the patient name, a third call sends the patient identification number, and so on. When using XML message based transactions, however, all of the information is sent in a single transaction.

The client 148 uses XML messaging wrapper 270 to create an XML representation and header section. The user enters data into each field on the form 252 using the keyboard 250. The entries may be stored in a temporary buffer or the memory 136. The user may press a Send or Enter key on the keyboard 250 to indicate when the form 252 is complete. It should be understood that the form 252 may have multiple pages that are not displayed on the display 130 all at the same time.

The client 148 writes the data in the agreed upon format to the data section of the XML tree. The XML message wrapper 270 creates the BSTR message and performs error checking. The first component 138 and the client 148 have agreement as to what should be in the data section, and thus XML Messaging wrapper 270 and 272 may be the same code.

Tags associated with the fields Name 254 and Patient ID 256 of the form 252 may be required; therefore, if no data is entered into these fields, an error is generated. For example, an error may be displayed in an upper portion 262 or a lower portion 264 of the display 130, indicating to the user that data must be entered. Also, tags may have a defined value type. The tag associated with Name 254 may be a string while the tag associated with Age 258 may be an integer. Therefore, if the user enters a letter into the Age 258 field, an error will be generated.

Once the error checking is satisfied, the client 148 sends the message to the first component 138. The first component uses XML messaging wrapper 272 to extract the message, and verifies the validity of the header and data sections. The first component 138 then commits the patient record to a patient database 266, which may be stored in the memory 150.

Optionally, the user may wish to modify a form, such as the form 252 to create a new patient, to include additional data or exclude data. For example, the user may wish to include the date of birth of the patient, but not the age. Therefore, the application can be configured to satisfy the user's requirements by modifying the code for XML messaging wrappers 270 and 272. The source code does not need to be modified.

In an alternate example, the user may wish to perform a back up of patient or system data. This functionality may be performed by the second component 140. The XML tree is created using XML messaging wrapper 274, which comprises the same functions and definitions for the data section of the message as XML messaging wrapper 276. The definition of the data section has been defined and agreed upon by the client 148 and the second component 140. Although the data section may be different and/or unique to each application, the header section for the messages created and sent to both the first and second components 138 and 140 may be the same. Optionally, one header may be defined for all applications within the system 5.

A form 268 is displayed on the display 130. For example, the form 268 allows the user to enter data identifying the files to be archived and/or allows the user to select the files by displaying a directory tree. The user also selects or inputs the location the files are to be archived to, such as drive 132. Once all data has been input, the client 148 completes the data section 222 with the appropriate data and sends the message to the second component 140.

Previously, the client 148 and second component 140 would send messages back and forth to negotiate what had to be done to complete the transaction. The second component 140 may have been configured to return a status message after receiving each call, greatly increasing the messaging traffic. With XML message based transactions, the second component 140 receives all of the information necessary to complete the transaction in the one message, and uses XML messaging wrapper 276 to extract the header and data information. When the transaction is complete, a single status message is returned to the client 148. The client 148 may display a message on the display 130 to notify the user that the transaction was or was not completed successfully. Therefore, less message traffic is generated, transaction integrity is increased, and the time required to complete a transaction is minimized.

A technical effect of an XML message based system is both improving transaction processing time and enforcing transaction integrity. A simple, lightweight messaging wrapper comprising XML is created that is decoupled from the application code, allowing easy modification and integration of software packages. At the same time, the time it takes for a transaction to execute is improved by reducing the number of calls needed to send a transaction to one call. Reducing the number of requests necessary to process a transaction makes transaction management more efficient and ensures transaction integrity.

While the invention has been described in terms of various specific embodiments, those skilled in the art will recognize that the invention can be practiced with modification within the spirit and scope of the claims.

What is claimed is:

1. A method for sending and receiving XML message based transactions between a client and software components of a medical imaging system, comprising:
   receiving a call having a free-form text based transactions request;
   using the received call to form a message;
   forming the message with a client and a first XML messaging wrapper, said message comprising a tag in a header section and a data section, wherein said data section includes at least one of a patient data or medical system data;
   sending said message to a first and second components, said first and second components configured to process different first and second sets of transactions that are associated with said medical imaging system, said first and second sets of transactions being non-acquisition related medical transactions;
   receiving said message with said first and second components, said first and second components reading said tag with associated XML messaging wrappers to determine a type of transaction based on said tag;
   verifying that said message contains data in said data section and a valid header in said header section; and
   executing a transaction based on said message with one of said first and second components.

2. The method of claim 1, said transaction further comprising at least two calls, said message comprising a text based representation of said at least two calls.

3. A method for sending and receiving XML message based transactions between a client and software components of a medical imaging system, comprising:
   receiving a call having a free-form text based transactions request;
   using the received call to form a message;
   forming the message with a client and a first XML messaging wrapper, said message comprising a tag in a header section and a data section;
   sending said message to first and second components, said first and second components configured to process different first and second sets of transactions that are associated with said medical imaging system, said first and second sets of transactions being non-acquisition related transactions, wherein a least one of said first and second components is configured to create a new patient record, perform measurements of anatomy, or store at least one of selected data and files to a selected drive;
   receiving said message with said first and second components, said first and second components reading said tag with associated XML messaging wrappers to determine a type of transaction based on said tag;
   verifying that said message contains data in said data section and a valid header in said header section; and
   executing a transaction based on said message with one of said first and second components.

4. The method of claim 1, further comprising defining said data section based on a function of said client and one of said first or second components.

5. The method of claim 1, wherein the software components of the medical imaging system comprise application code, said forming step further comprising:
creating an XML representation with said first XML messaging wrapper, said first XML messaging wrapper being stored decoupled from said client, the XML messaging wrapper further decoupled from the application code of the software components of the medical imaging system;
building said header section and said data section based on said XML representation; and
generating a text string based on said XML representation, said text string comprising said message.

6. The method of claim 1, said receiving step further comprising:
creating an XML representation with said XML messaging wrapper associated with said first or second component that will execute said transaction, said XML messaging wrappers being stored decoupled from said first and second components;
reading said header section; and
reading said data section, said executing step being based on said data section.

7. The method of claim 1, said header section further comprising a plurality of tags, a first subset of said tags being required, a second subset of said tags comprising a value type, said receiving step further comprising:
reading said header section with said XML messaging wrapper of one of said first and second components; and
generating an error message after the reading step when a required tag is one of missing and incorrect value type said error message being displayed on a display or logged in a file.

8. The method of claim 1, said verifying step further comprising:
reading said data section with said XML messaging wrapper of one said first and second components;
generating an error message when said data section is one of empty and includes an incorrect value type; and
sending said message to said client.

9. The method of claim 1, said header section further comprising tags, each of said tags defining a function, said tags comprising at least one of envelope, header, version, sender name, sender identification, receiver name, receiver identification, checksum, and time sent.

10. The method of claim 1, said forming step further comprising writing said header section and said data section based on an XML message definition.

11. A system for sending and receiving XML message based transactions within an ultrasonic imaging system, comprising:
a front-end comprising components for transmitting ultrasonic signals and receiving echoes based on said ultrasonic signals;
processing architecture comprising components for processing said echoes;
an input device for inputting a free-form text based transactions request; and
a computer comprising a microprocessor and a memory, said memory storing the free-form text input from said input device, said computer further comprising a storage device for storing software programs, said software programs comprising a client and a client XML messaging wrapper the client XML messaging wrapper using the free-form text input to generate XML message based transactions for the ultrasonic imaging system, said client XML messaging wrapper being stored decoupled from said client, said software programs further comprising at least a first component and a first XML messaging wrapper for receiving and processing said XML message based transactions, wherein said processing comprises verify that said XML message based transactions contain data in a data section and a valid header in a header section of received messages, said first XML messaging wrapper being stored decoupled from said first component, said client XML messaging wrapper and said first XML messaging wrapper comprising functions for reading and writing data in XML format to create and process a first set of XML message based transactions.

12. The system of claim 11, said software programs further comprising second and third components associated with second and third XML messaging wrappers, respectively, that are stored decoupled from said second and third components, each of said first, second and third components performing functions different from one another, each of said first, second, and third XML messaging wrappers comprising functions different with respect to each other.

13. The system of claim 11, said software programs further comprising a second component and a second XML messaging wrapper that is stored decoupled from said second component, said client XML messaging wrapper and said second XML messaging wrapper further comprising functions for reading and writing data in XML format to create and process a second set of XML message based transactions, said first and second sets of XML message based transactions being different with respect to each other.

14. The system of claim 11, wherein said first set of XML message based transaction is associated with creating a new patient record, performing measurements of anatomy, or storing at least one of selected data and files to a selected drive.

15. A method for sending and receiving XML message based transactions within a medical imaging system, comprising:
receiving a call having a free-form text based transactions request;
using the received call to build a message;
building a message with a client and an XML messaging wrapper to be sent from said client to a first software component, said message requesting completion of a transaction, within the medical imaging system, said message comprising a header section and a data section formed of XML tags, wherein said data section includes patient identification data, said XML messaging wrapper comprising functions for reading and writing data in XML format, said XML messaging wrapper being stored decoupled from said client;
verify that said message contains data in said data section and a valid header in said header section;
creating a text based representation of said message; and
sending said text based representation to said first software component.

16. The method of claim 15, further comprising configuring said data section based on an application of said first software component.

17. The method of claim 15, further comprising configuring a data section of a first message based on an application of said first software component, said first message being built with a first XML messaging wrapper, configuring a data section of a second message based on an application of a second software component, said second message being built with a second XML messaging wrapper that is different and stored separated from said first XML messaging wrapper, said data sections based on said first and second software components being different.

18. The method of claim 15, further comprising:
creating an XML representation with an XML messaging wrapper associated with said first software component;
reading said header section of said text based representation into said XML representation; and
determining an action to be taken by said first software component based on said header section.

19. The method of claim 15, further comprising:
completing said transaction with said first software component based on said text based representation; and
forming a status message based on a result of said completing step, said first software component sending said status message to said client.

20. The method of claim 15, further comprising;
storing said XML messaging wrapper in a first location;
storing said client in a second location;
storing said first software component in a third location; and
storing an XML messaging wrapper associated with said first software component in a fourth location, said first, second, third and fourth locations being different.

21. The method of claim 1, wherein the free-form text based transactions request comprised at least one of an unstructured text, a sentence, or a natural language input.

\* \* \* \* \*